United States Patent [19]
Underiner et al.

[11] Patent Number: 5,473,070
[45] Date of Patent: Dec. 5, 1995

[54] SUBSTITUTED LONG CHAIN ALCOHOL XANTHINE COMPOUNDS

[75] Inventors: Gail Underiner, Brier; David Porubek, Edmonds; J. Peter Klein, Vashon Island; Paul Woodson, Bothell, all of Wash.

[73] Assignee: Cell Therapeutics, Inc., Seattle, Wash.

[21] Appl. No.: 976,353

[22] Filed: Nov. 16, 1992

[51] Int. Cl.[6] .................. C07D 473/04; A61K 31/52
[52] U.S. Cl. ............................................ 544/267; 514/263
[58] Field of Search ............................. 544/267; 514/263

[56] References Cited

U.S. PATENT DOCUMENTS

| | | | |
|---|---|---|---|
| 3,737,433 | 3/1983 | Mohler et al. | 544/271 |
| 4,515,795 | 7/1985 | Hinze et al. | 544/267 |
| 4,599,414 | 7/1986 | Sugimoto et al. | 544/269 |
| 4,612,315 | 9/1986 | Jacobson et al. | 544/269 |
| 4,833,146 | 5/1989 | Gebert et al. | 514/263 |

Primary Examiner—Mukund J. Shah
Assistant Examiner—P. K. Sripada
Attorney, Agent, or Firm—Stephen Faciszewski; Jeffrey B. Oster

[57] ABSTRACT

There is disclosed compounds and pharmaceutical compositions comprising compounds of the formula:

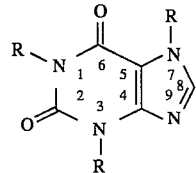

FORMULA 1 wherein each of one or two R is independently

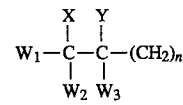

wherein n is an integer from 7 to 20, at least one of X or Y is —OH and if one of X or Y is —OH then the other X or Y is H, $CH_3$, $CH_3$—$CH_2$, $CH_3$—$(CH_2)_2$—, or $(CH_3)_2$—$CH_2$—, and $W_1$, $W_2$, and $W_3$ is independently H, $CH_3$, $CH_3$—$CH_2$, $CH_3$—$(CH_2)_2$—, or $(CH_3)_2$—$CH_2$—, and wherein the alkyl groups may be substituted by a hydroxyl, halo or dimethylamino group and/or interrupted by an oxygen atom, H or alkyl (1–4C), including resolved enantiomers and/or diastereomers, salts and mixtures thereof. In particular, the compounds lower elevated levels of unsaturated, non-arachidonate phosphatidic acid (PA) and diacylglycerol (DAG) derived from said PA within seconds of the primary stimulus and their contact with said cells. The modulatory effect depends on the nature of the target cell and the stimulus applied.

12 Claims, 6 Drawing Sheets

SUBSTITUTED LONG CHAIN ALCOHOL XANTHINE COMPOUNDS

TECHNICAL FIELD OF THE INVENTION

The invention relates to a class of substituted long chain alcohol xanthine compounds that are effective agents to modulate cellular responses to stimuli. More specifically, the inventive compounds have at least one hydroxyl-containing long chain substituent bonded to a ring nitrogen. The inventive compounds are useful antagonists to control intracellular levels of specific sn-2 unsaturated phosphatidic acids and corresponding phosphatidic acid-derived diacylglycerols which occur in response to cellular proliferative stimuli.

BACKGROUND ART

Pentoxifylline (1-(5-oxohexyl)-3,7-dimethylxanthine), abbreviated PTX, is a xanthine derivative which has seen widespread medical use for the increase of blood flow. PTX is disclosed in U.S. Pat. Nos. 3,422,307 and 3,737,433. Metabolites of PTX were summarized in Davis et al., *Applied Environment Microbiol.* 48:327, 1984. A metabolite of PTX is 1-(5-hydroxyhexyl)-3,7-dimethylxanthine, designated M1. M1 was also disclosed as increasing cerebral blood flow in U.S. Pat. Nos. 4,515,795 and 4,576,947. In addition, U.S. Pat. Nos. 4,833,146 and 5,039,666 disclose use of tertiary alcohol analogs of xanthine for enhancing cerebral blood flow.

Furthermore. U.S. Pat. No. 4,636,507 describes an ability of PTX and M1, to stimulate chemotaxis in polymorphonuclear leukocytes in response to a stimulator of chemotaxis. PTX and related tertiary alcohol substituted xanthines inhibit activity of certain cytokines to affect chemotaxis (U.S. Pat. No. 4,965,271 and U.S. Pat. No. 5,096,906). Administration of PTX and GM-CSF decrease tumor necrosis factor (TNF) levels in patients undergoing allogeneic bone marrow transplant (Blanco et al., *Blood* 76: Supplement 1 (522A), 1990). Reduction in assayable levels of TNF was accompanied by reduction in bone marrow transplant-related complications. However, in normal volunteers, TNF levels were higher among PTX recipients. Therefore, elevated levels of TNF are not the primary cause of such complications.

Therefore, there is a need in the art to discover effective therapeutic compounds that are safe and effective for human or animal administration and that can maintain cellular homeostasis in the face of a variety of inflammatory stimuli. The present invention was made in a process of looking for such compounds.

SUMMARY OF THE INVENTION

We have found that the compounds described herein can be used to maintain homeostasis of a large variety of target cells in response to a variety of stimuli. In addition, the inventive compounds and compositions are suitable for normal routes of therapeutic administration and permit effective dosages to be provided.

The invention is directed to the use of substituted xanthines containing at least one hydroxyl derivatized side chain of at least 9 carbon atoms in length in modulating cellular response to external or in situ primary stimuli, as well as to specific modes of administration of such compounds in effective amounts.

The inventive compounds comprise compounds and pharmaceutical compositions comprising compounds of the formula:

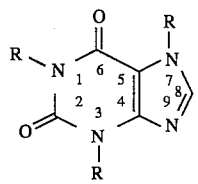

FORMULA 1 wherein each of one or two R is independently

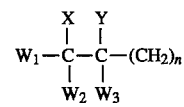

wherein n is an integer from 7 to 20, at least one of X or Y is —OH and if one of X or Y is —OH then the other X or Y is H, $CH_3$, $CH_3$—$CH_2$, $CH_3$—$(CH_2)_2$—, or $(CH_3)_2$—$CH_2$—, and $W_1$, $W_2$, and $W_3$ is independently H, $CH_3$, $CH_3$—$CH_2$, $CH_3$—$(CH_2)_2$—, or $(CH_3)_2$—$CH_2$—, and wherein the alkyl groups may be substituted by a hydroxyl, halo or dimethylamino group and/or interrupted by an oxygen atom, H or alkyl (1–4C), including resolved enantiomers and/or diastereomers, salts and mixtures thereof. Preferably, n is from 7–10 and both X and Y are OH and each W is H or $CH_3$.

The present invention further comprises a method for modulating an immune response or a cellular response to external or in situ primary stimuli comprising administering an effective amount of a compound of Formula 1. More specifically, the invention is directed to methods to decrease proliferation of tumor cells in response to an activated oncogene; to stimulate hematopoiesis in the presence of agents which inhibit hematopoiesis, such as chemotherapeutic agents; to suppress the activation of T-cells in the presence of antigen and the secretion of antibodies by B-cells in the presence of antigen; to suppress the activation of macrophage or endothelial cells by endotoxins, TNF, IL-1 or GM-CSF; to enhance the resistance of mesenchymal cells to tumor necrosis factor (TNF); to inhibit the proliferation of smooth muscle cells endothelial cells, fibroblasts and other cell types in response to growth factors, such as PDGF-AA, BB, FGF, EGF, etc.; to inhibit the activation of T-cells and viral replication in response to human immunodeficiency virus; to inhibit the proliferation of kidney mesangial cells in response to IL-1; to prevent suppression of Steel factor (also called stem cell factor, mast cell growth factor and kit ligand), G-CSF, oncostatin M or IL-6 in bone marrow stromal cells in response to TNF; to suppress expression of adhesion molecules in endothelial cells and suppress adhesion of inflammation cells to endothelial cells; to suppress proliferation of kidney mesangial cells in response to IL-1, mip-1α, PDGF or FGF; to prevent toxicity in kidney glomerular or tubular cells in response to cyclosporin A or amphotericin B; to prevent cytotoxic effects in gastrointestinal or pulmonary epithelial cells in response to a cytotoxic drug or radiation; to enhance the antitumor effects in tumor cells in response to a nonalkylating antitumor agent; to suppress the production of metalloproteases in synovial cells, other fibroblasts and a glomerular epithelial cell in response to inflammatory stimuli, such as TNF, IL-1 and the like, to inhibit production of osteoclast-activating factor (OAP) by osteoclasts in response to IL-1; to inhibit degranulation of mast cells and basophils in response to IgE; to modulate signal transduction of the neurotransmitters epinephrine and acetylcholine in neural pathways utilizing these transmitters, block activation of platelet activating factor in inflammation cells, block release of TNF and IL-1 in various cell types in response to inflammatory stimuli, block activation and proliferation of lymphocytes and other cell types to IL-1 and IL-2, and the like including the clinical manifestations of these cellular events, comprising administering an effective amount of a compound of Formula 1.

In still another aspect, the invention is directed to a pharmaceutical composition comprising a compound of Formula 1 and an effective amount of an agent which reduces the activity of the enzyme P-450, such as a quinolone, to increase the pharmacokinetic half-life of a compound of Formula 1.

BRIEF DESCRIPTION OF THE DRAWINGS

FIGS. 5A–5D show the flow cytometric frequency histograms plotting cell number versus relative fluorescence intensity. FIG. 5A is non-TNF induced expression of VCAM (% of cells in gate A is 0.4%). FIG. 5B shows cells treated with TNF (% of cells in gate B is 34.5%). FIG. 5C shows cells treated with CT1559 (0.25 mM) one hour prior to TNF addition (% of cells in gate C is 24%). FIG. 5D is cells treated with PTX for comparison (% of cells in gate D is 36.8%).

FIG. 6 shows an analysis of mean fluorescence intensity of cells analyzed by flow cytometry. The mean fluorescence levels were decreased by CT 1559 treatment by 1.7 fold from control levels (TNF treatment, no drug).

DETAILED DESCRIPTION OF THE INVENTION

Figure 1:
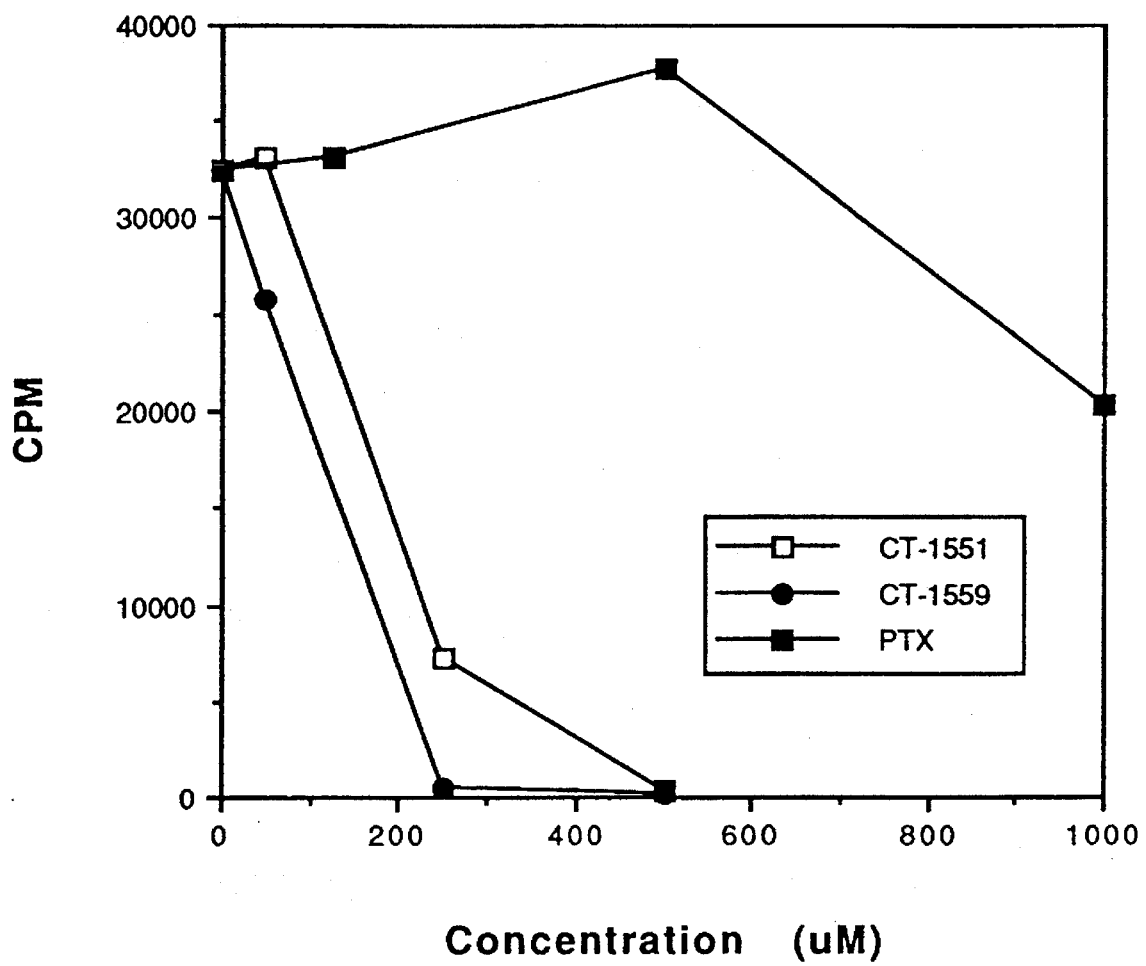
FIG. 1 shows a mixed lymphocyte reaction of PTX and two inventive compounds CT1551 (racemate N-(8-hydroxynonyl)theobromine) and CT1559 (N-(10-hydroxydecyl)theobromine). The mixed lymphocyte reaction shows a proliferative response of PBMC (peripheral blood mononuclear cells) to allogeneic stimulation determined in a two-way mixed lymphocyte reaction. Each of the inventive compounds tested was more effective and more potent than PTX in this immune modulating activity assay procedure.

The invention is directed to a defined genus of compounds which can control cellular behavior by a particular phase of a secondary messenger pathway system (Bursten et al. *J. Biol. Chem.* 266:20732, 1991 ). The second messengers are lipids or phospholipids and use the following abbreviations:

PE=phosphatidyl ethanolamine
LPE=lysophosphoethanolamine
PA=phosphatidic acid
LPA=lysophosphatidic acid
DAG=diacylglycerol
LPLD=lysophospholipase-D
LPAAT=lysophosphatidic acid acyl transferase
PAPH=phosphatidic acid phosphohydrolase
PLA2=phospholipase A-2.
PLD=phospholipase D
PAA=phosphoarachidonic acid
PLA-2=phospholipase A2
PC=phosphatidyl choline "remodeled" PA, cyclic pathway=PAA, LPA, PA and DAG intermediates substituted with L-saturated, 2-linoleoyl or 1,2-dileolyl/1,2-sn-dilinoleoyl at the indicated sn-1 and sn-2 positions.

"Classical PI Pathway"=PI, DAG, PA intermediates substituted with 1-stearoyl, 2-arachidonoyl fatty acyl side chains.

"PLD-generated PA"=PE, PC, LPA, PA and DAG intermediates substituted with, e.g., 1,2-sn-dioleoyl-, 1-alkyl, 2-linoleoyl-, and 1-alkyl, 2-docosahexaneoyl-side chains.

Lysophosphatidic acid transferase (LPAAT) effects the synthesis of phosphatidic acid (PA) from lysophosphatidic acid (LPA) by incorporation of an acyl group from acyl CoA. Hydrolysis of the phosphate moiety by PA phosphohydrolase (PAPH) results in the formation of DAG. These aspects of the pathway appear to be activated immediately (within a minute) upon stimulation by a primary stimulus (e.g., a cytokine such as interleukin-1 or TNF) acting at a receptor on a cellular surface. An immediate detectable effect is an elevation of levels of PA and DAG. Administration of the compounds of the invention reverse this elevation.

The compounds of the invention, include inhibitors of subspecies of LPAAT in PAPH enzymes with substrate specificity for intermediates with 1,2-diunsaturated and 1-alkyl, 2-unsaturated subspecies. One representative example of such an inhibitor (although not within the genus defined by Formula 1) is PTX. PTX blocks PAPH in a specific activation pathway that does not involve PI but rather derives from a PA that is largely composed of 1,2-diunsaturated and 1-alkyl,2-unsaturated subspecies. This was shown, for example, by the demonstration that human mesangial cells stimulated with TNF produce DAG from PI and regenerate PI in the absence and the presence of PTX. In the latter system there is no evidence to suggest that PA or DAG are derived from sources other than PI. It should be emphasized that the compounds of the invention affect that subset of PAPH and LPAAT that relates to substrates with unsaturated fatty acids other than arachidonate in the sn-2 position, not the housekeeping forms of these enzymes that serve the PI pathway.

In Vitro Assays for Physiologic and Pharmacologic Effects of the Invention Compounds Various in vitro assays can be used to measure effects of the inventive compounds to module immune activity and have antitumor activity using a variety of cellular types. For example, a mixed lymphocyte reaction (MLR) provides a valuable screening tool to determine biological activity of each inventive compound. In the MLR, PBMCs (peripheral blood mononuclear cells) are obtained by drawing whole blood from healthy volunteers in a heparinized container and diluted with an equal volume of hanks balanced salt solution (HBSS). This mixture is layered on a sucrose density gradient, such as a Ficoll-Hypaque® gradient (specific gravity 1.08), and centrifuged at 1000×g for 25 minutes at room temperature or cooler. PBMC are obtained from a band at a plasma-Ficoll interface, separated and washed at least twice in a saline solution, such as HBSS. Contaminating red cells are lysed, such as by ACK lysis for 10 min at 37° C., and the PBMCs are washed twice in HBSS. The pellet of purified PBMCs is resuspended in complete medium, such as RPMI 1640 plus 20% human inactivated serum. Proliferative response of PBMC to allogeneic stimulation is determined in a two-way MLR performed in a 96-well microtiter plate. Briefly, approximately $10^5$ test purified PBMC cells in 200 µl complete medium are co-cultured with approximately $10^5$ autologous (control culture) or allogeneic (stimulated culture) PBMC cells, wherein the allogeneic cells are from HLA disparate individuals. Varying doses of compounds (drug) are added at the time of addition of cells to the microtiter plate. The cultures are incubated for 6 days at 37° C. in a 5% $CO_2$ atmosphere. At the conclusion of the incubation tritiated thymidine is added (for example, 1 µCi/well of 40 to 60 Ci/mmole) and proliferation determined by liquid scintillation counting.

A thymocyte costimulator assay is conducted to evaluate the inventive compounds to inhibit activation and proliferation of thymocytes caused by stimulation with Con A and interleukin-1 (IL-1), or interleukin-1 (IL-2). Thymuses are obtained from mice (e.g., female Balb/C mice) and the thymuses are removed and dissociated into culture media (e.g., RPMI 1640 without serum supplementation). The dissociated thymus tissue and cell suspension is transferred to centrifuge tubes and allowed to settle, washed with HBSS and resuspended in serum-supplemented culture media (e.g., RPMI 1640 with 10% fetal calf serum). Any contaminating red cells are lysed, and viable cells are resuspended and counted. Thymocytes are plated (e.g., 96-well plates at a density of $2\times10^5$ cells/well) and a stimulating agent, such as Con A, IL-1 (e.g., IL-1α) or IL-2 is added to the well. The cells are incubated for 4 days at 37° C. On the fourth day, the cells are pulsed with tritiated thymidine and cell proliferation determined. Inventive compounds are added at the time of stimulating agent addition.

Each inventive compound is investigated for cytotoxicity to determine appropriate doses for biological activity assays and to prevent cytotoxic reactions in in vitro assays when characterizing activity. Cells (e.g., NIH-3T3, Ras transformed 3T3 cells, malignant melanoma LD2 cells, etc.) are added to microtiter plates and drug is added about two days after plating. Cell viability is determined using a fluorescent viability stain (2',7'-bis-(2-carboroxyethyl)-5-(and -6)-carboxyfluorescein acetoxymethyl ester, BCECF excitation 488 nm and emission 525 nm) 24, 48 or 72 hours after addition of the drug.

Another assay for measuring activity of the inventive compounds involves determining PDGF (platelet derived growth factor) proliferative response using human-derived stromal cells. Human stromal cells are plated (e.g., about 2000 cells per well) in defined media (e.g., 69% McCoy's, 12.5% fetal calf serum, 12.5% horse serum, 1% antibiotics, 1% glutamine, 1% vitamin supplement, 0.8% essential amino acids, 1% sodium pyruvate, 1% sodium bicarbonate, 0.4% non-essential amino acids and 0.36% hydrocortisone). Two to three days later, the stromal cells are starved in serum-free media. Twenty four hours later, the cells are treated with a stimulating agent, such as PDGF-AA, PDGF-BB or basic FGF (fibroblast growth factor) with or without IL-1α or TNF, and tritiated thymidine. Cell proliferation is determined by liquid scintillation counting.

A B-cell proliferation assay determines the effect of the inventive compounds on inhibiting proliferation of stimulated B-cells, stimulated by an anti-mu antibody (40 µg/ml), IL-4 or PMA (2.5 nM). Ramos B-cell tumor cells or murine splenocytes can be incubated with a stimulating agent, an inventive compound and tritiated thymidine to measure inhibition of cell proliferation caused by the stimulating agent.

Drug inhibitory activity can also be measured by determining levels of vascular cell adhesion molecule (VCAM) in stimulated cells. Early passage human umbilical vein endothelial cells (HUVEC) (obtained from commercial suppliers such as Cell Systems, Inc. or Clonetics) are cultured in media (e.g., Hepes buffered media, Cell Systems) containing 10% fetal bovine serum, and supplemented with a stimulating agent, such as fibroblast growth factor (acidic FGF, Cell Systems, Inc.) or TNF. The cells are plated into wells of a microtiter plate (e.g., $5\times10^4$ per well) and allowed to incubate at 37° C. for 72 hrs. The resting cells are removed (e.g., 20–30 min treatment with 0.4% EDTA), washed in media (e.g., phosphate buffered saline plus 0.1% bovine serum albumin with 0.01% sodium azide) and labeled on ice with a monoclonal antibody ("first antibody") recognizing human VCAM (e.g., 1 µg of a murine monoclonal antibody recognizing human VCAM Genzyme). After 60 min on ice, the cells are washed (preferably twice) with cold wash media and incubated with an antibody that recognizes the first antibody, (e.g., 1 µg of goat anti-mouse IgG conjugated with phycoerythrin, CalTag, Inc.). After 30 min on ice, the cells are washed twice and analyzed on a flow cytometer (Coulter Elite®) at appropriate emission and excitation wavelengths (e.g., for phycoerythrin use excitation at 488 nm and emission at 525 nm).

One in vitro assay measures inhibition of the relevant enzymes lysophosphatidic acid acyltransferase (LPAAT) and phosphatidic acid phosphoryl hydrolase (PAPH). The assay involves incubating of target cells with a primary stimulus (e.g., a variety of cytokines, growth factors, oncogene products, putative therapeutic agents, irradiation, viral infection, toxins, bacterial infection and the products thereof, and any stimulus which, if not counteracted, has a deleterious effect on the target cell) in the presence or absence of an inventive compound at varying dosage levels. Target cells include, for example, subcellular entities, such as, microsomes derived from mesenchymal and/or ectodermal cells, particularly microsomes from marrow stromal cells or human or rat mesangial cells; microsomes or synaptosomes derived from bovine brain; plasma membrane-enriched microsomes or plasma membranes derived as described in Bursten et al. (*J. Biol. Chem.* 226:20732–20743, 1991 ) detergent-solubilized microsomes; synaptosomes, and membranes or other cell preparations solubilized using, for example, NP-40, Miranal, SDS or other neutral detergents; and detergent-solubilized or further purified preparations of cell proteins, including the proteins LPAAT and/or PAPH. After incubation for short periods of time, cell lipids are extracted and assayed by thin layer chromatography according to standard procedures. Briefly, lipids are extracted using, for example, chloroform:methanol 2:1 (v/v), and the extracts are then subjected to HPLC as described in Bursten and Harris, *Biochemistry* 30:6195–6203, 1991. A Rainin mu-Porasil column is used with a 3:4 hexane:propanol organic carrier and a 1–10% water gradient during the first 10 minutes of separation. Detection of the peaks in the elution pattern is by absorption in the range of ultraviolet which detects isolated double bonds. The relevant peaks of unsaturated PA and DAG are shown in the elution pattern. It is important to note that the assay method permits discrimination between various forms of PA and DAG so that those relevant to the pathway affected by the (R) or (S) compounds of the invention can be measured directly. Confirmation of the nature of the acyl substituents of these components is accomplished using fast-atom bombardment mass spectroscopy. Thus, the relevant unsaturated (non-arachidonic) PA and DAG subspecies may be detected. The time periods employed are 5–60 seconds after stimulation with the primary stimulus, such as a cytokine. This technique permits assessment of the levels of various lipid components as a function of time.

Compounds of the Invention

The inventive compounds comprise compounds and pharmaceutical compositions comprising compounds of the formula:

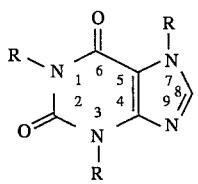

FORMULA 1 wherein each of one or two R is independently

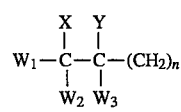

wherein n is an integer from 7 to 20, at least one of X or Y is —OH and if one of X or Y is —OH then the other X or Y is H, $CH_3$, $CH_3$—$CH_2$, $CH_3$—$(CH_2)_2$—, or $(CH_3)_2$—$CH_2$—, and $W_1$, $W_2$, and $W_3$ is independently H, $CH_3$, $CH_3$—$CH_2$, $CH_3$—$(CH_2)_2$—, or $(CH_3)_2$—$CH_2$—, and wherein the alkyl groups may be substituted by a hydroxyl, halo or dimethylamino group and/or interrupted by an oxygen atom, H or alkyl (1–4C), including resolved enantiomers and/or diastereomers, salts and mixtures thereof. Preferably, n is from 7–10 and both X and Y are OH and each W is H or $CH_3$.

Those embodiments are preferred wherein a single alkyl amine substituent (e.g., R) is at position 1 of this xanthine nucleus, or where the alkyl amine substituents are at position 1 and 7. Also preferred, are those compounds of the invention wherein a single R substituent, which is a long chain alcohol or diol substituent, is at position 7 of the xanthine nucleus.

The remaining R substituents are independently H, alkyl (1–6C), alkenyl (1–6C) or benzyl wherein the alkyl or alkenyl substituents may be further substituted with a hydroxy group, halo, dimethylamine and/or may be interrupted by an oxygen atom. Suitable embodiments for the remaining R groups include methyl, ethyl, isopropyl, n-propyl, isobutyl, n-butyl, t-butyl, 2-hydroxyethyl, 3-hydroxypropyl, 3-hydroxy-n-butyl, 2-methoxyethyl, 4-methoxy-n-butyl, 5-hydroxyhexyl, 2-bromopropyl, 3-dimethylaminobutyl, 4-chloropentyl, and the like. Particularly preferred substituents are ethyl, methyl, or H; and especially methyl or H. Particularly preferred compounds of the invention are also exemplified herein.

The compounds of the invention may be provided as enantiomeric or diastereomeric mixtures or in resolved or partially resolved forms. Standard procedures are used for resolution of optical isomers. It is contemplated that the different enantiomeric variants (e.g., stereoisomers and chiral forms) of the xanthines will have different drug activities, based upon their differential ability to inhibit PAPH and LPAAT. By an optical isomer substantially free of the corresponding enantiomer and/or diastereomers is meant at least about 85% relevant optical isomer, preferably at least about 95% relevant optical isomer and especially at least about 99% or higher relevant optical isomer, but most preferably where the amount of other optical forms is undetectable.

The inventive compounds were found to have activity, wherein potency is a function of chain length. For example, when n is 2 or less, the compounds have no activity in the relevant assays. When n is 3 or 4, there is a small amount of activity in the proliferation inhibition assays described herein. When n is 6 there is moderate activity and this activity increases exponentially (on a potency basis) when n is increased to 7 and greater. This steeply rising curie is disclosed for illustrated compounds wherein n is 7 or 8.

The present invention further comprises a pharmaceutical composition comprising one or a plurality of compounds of Formula I and a pharmaceutically acceptable carrier or excipient. The cells to be treated with an inventive compound or inventive pharmaceutical composition may either be contacted with the compound of the invention in vitro culture, in an extracorporeal treatment, or by administering the compound of the invention or pharmaceutical composition to a subject whose cells are to be treated.

Illustrative compounds of the invention include both racemic mixture and R and S enantiomers of the following compounds (which are racemic mixtures):
CT1551 N-(8-hydroxynonyl)theobromine
CT1552 N-(9-hydroxydecanyl)theobromine
CT1559 N-(10-hydroxydecanyl)theobromine
CT1561 N-(8,9-dihydroxynonyl)theobromine
CT1564 N-(9,10-dihydroxydecyl)theobromine Uses of the Invention Compounds and Pharmaceutical Formulations The compounds of the invention provide a mechanism to maintain homeostasis in cells contacted by primary stimuli through mitigating the effects of these primary stimuli on the secondary signaling pathways invoked within seconds of the primary stimulus.

For example, the compounds of the invention are used in connection with patients undergoing bone marrow transplantation (BMT), regardless of whether the BMT is matched allogeneic, mismatched allogeneic, or autologous. Patients receiving autologous transplants are aided by treatment with compounds of the invention even though they do not necessarily need to be administered immunosuppressive agents, since they do not develop graft-versus-host disease (GVHD). However, the toxic effect of the chemotherapy or radiation therapy used in connection with the disease, in response to which the transplantation has been performed, constitutes a negative stimulus with regard to the patients' cells.

In general, all patients undergoing BMT require doses of chemotherapy with or without total body irradiation that exceed the lethal dose for normal bone marrow recovery. This provides the rationale for using either stored patient marrow or donor marrow to rescue the patient. In general, chemotherapy and radiation are delivered to the patient for 7–10 consecutive days before the new or stored bone marrow is infused. The day on which the marrow is given to the patient is referred to as day 0 of the transplant. Previous days on which the patient received chemo/radiation are designated by negative numbers. Subsequent days are referred to by positive numerals.

The median time in which negative responses in BMT recipients occurs is within the first 100 days after transplant. Therefore, statistically, if patients survive through day 100, their chances for continued survival are significantly enhanced. Compounds of Formula 1 are able to increase the percentage of patients who survive. The percentage of fatalities within the first 100 days that is considered acceptable is 15–20% for "good risk" patients and 30–40% for "high risk". These fatalities are due to the direct effects of high doses of chemo/radiation; in addition, GVHD contributes to the death rate in allogeneic marrow recipients.

Other indications for which it is useful to administer the compounds of the invention include the presence of a tumor burden, a hormone-related disorder, a neurological disorder, an autoimmune disease, inflammation, restenosis, hypertension, unwanted immune response, viral infection, nephritis, mucositis, and various allergic responses. Prevention of allergic responses include prevention of acute allergic response and thus moderation or prevention of rhinorrhea, serious drainage, diffuse tissue edema, and generalized pruritus. Other symptoms of chronic allergic response include, as well as the foregoing, dizziness, diarrhea, tissue hyperemia, and lacrimal swelling with localized lymphocyte infiltration. Allergic reactions are also associated with leukotriene release and the distal effects thereof, including asthmatic symptoms including development of airway obstruction, a decrease in FEV 1, changes in vital capacity, and extensive mucus production.

Other suitable subjects for the administration of compounds of the invention, include patients being administered toxic agents for the treatment of tumors, such as chemotherapeutic agents or irradiation therapy, as well as treatment with biological response modifiers such as IL-2 and tumor suppressing cells such as lymphokine activated killer cells (LAK) and tumor-infiltrating lymphocytes (TIL cells); patients suffering from neoplasias generally, whether or not otherwise treated including acute and chronic myelogenous leukemia, hairy cell leukemia, lymphomas, megakaryocytic leukemia, and the like; disease states caused by bacterial, fungal, protozoal, or viral infection; patients exhibiting unwanted smooth muscle cell proliferation in the form of, for example, restenosis, such as patients undergoing cardiac surgery; patients who are afflicted with autoimmune diseases, thus requiring deactivation of T and B cells, and patients who have neurological disorders.

The compounds of the invention further are able to decrease the enhanced levels of a relevant PA and DAG resulting from stimulation of synaptosomes with acetylcholine and/or epinephrine. This suggests that the effects of the compounds of the invention are to both enhance the release of inhibitory neural transmitters such as dopamine, and to modulate the distal "slow current" effects of such neurotransmitters.

Thus, the drugs of the invention are also useful to raise the seizure threshold, to stabilize synapses against neurotoxins such as strichnine, to potentiate the effect of anti-Parkinson drugs such as L-dopa, to potentiate the effects of soporific compounds, to relieve motion disorders resulting from administration of tranquilizers, and to diminish or prevent neuron overfiring associated with progressive neural death following cerebral vascular events such as stroke. In addition, the compounds of the invention are useful in the treatment of norepinephrine-deficient depression and depressions associated with the release of endogenous glucocorticoids, to prevent the toxicity to the central nervous system of dexamethasone or methylprednisolone, and to treat chronic pain without addiction to the drug. Further, the compounds of the invention are useful in the treatment of children with learning and attention deficits and generally improve memory in subjects with organic deficits, including Alzheimer's patients.

While dosage values will vary, therapeutic efficacy is achieved when the compounds of the invention are administered to a human subject requiring such treatment as an effective oral, parenteral, or intravenous sublethal dose of about 200 mg to about 5000 mg per day, depending upon the weight of the patient. A particularly preferred regimen for use in treating leukemia is 4–50 mg/kg body weight. It is to be understood, however, that for any particular subject, specific dosage regimens should be adjusted to the individual's need and to the professional judgment of the person administering or supervising the administration of the inventive compounds.

Coadministration With a P-450 Inhibitor

The coadministration in vivo of the compounds of the invention along with an inhibitor of P-450 results in an enhanced effect due to a longer half life of the inventive compounds. This in vivo effect is due to inhibition of a degradation pathway for the compounds of the invention; in particular, dealkylation at the N7 position of the xanthine ring. For example, NIH3T3-D5C3 cells can be used to compare effects of a compound of Formula 1 alone or in combination with a P-450 inhibitor by comparing transformation phenotype control, incubation with a compound of Formula 1 alone, and coincubation of a compound of Formula 1 with the P-450 enzyme inhibitor.

Compounds that inhibit P-450 include, for example, (mg range daily dosage) propranolol (20–100), metaprolol (20–100); verapamil (100–400), diltiazem (100–400), nifedipine (60–100); cimetidine (400–2,400); ciprofloxacin (500–2000), enoxacin (500–2,000), norfloxacin (500–2000), ofloxacin (500–2,000), pefloxacin (500–2,000); erythromycin (100–1,000), troleandomycin (100–1,000); ketoconizole (100–2,000), thiabenzadole (100–1,000); isoniazid (100–1000); mexiletine (100–1,000); and dexamethasone (1–100 mg).

For combination therapy, the compounds of the invention and a P-450 inhibitor can be administered individually or in a single composition. A suitable formulation will depend on the nature of the disorder to be treated, the nature of the medicament chosen, and the judgment of the attending physician. In general, the inventive compounds are formulated either for injection or oral administration, although other modes of administration such as transmucosal or transdermal routes may be employed. Suitable formulations for these compounds can be found, for example, in *Remington's Pharmaceutical Sciences* (latest edition), Mack Publishing Company, Easton, Pa.

Depending on the compound of Formula 1 selected, the level of dosage can be appreciably diminished by coadministration of a P-450 inhibitor, such as the quinolone. Alternatively, a strong synergistic effect may be obtained with such a quinolone.

The invention is illustrated by the following examples which should not be regarded as limiting the invention in any way. In these examples PTX means pentoxifylline.

Example 1

This example illustrates a method for synthesis of CT1551 (1-(8 -hydroxynonyl)-3,7-dimethylxanthine). The synthesis began with a solution of 8-nonene-1-ol (3.52 mmol, 0.5 g) in 30 ml of dichloromethane. Methanesulfonyl chloride (3.52 mmol, 0.4 g, 270 µl) was added with stirring at 0° C., followed by an addition of triethylamine (5.28 mmol, 0.534 g, 736 µl). The mixture was warmed to room temperature over an hour and then was poured into 50 ml of saturated aqueous sodium bicarbonate solution. The organic layer was washed with an equal volume of brine, dried over magnesium sulfate, filtered and the solvent evaporated to give a mesylate, which was taken up in 10 ml of DMSO (dimethylsulfoxide).

A mixture of theobromine (3.52 mmol, 0.63 g) stirring in 20 ml DMSO was added to sodium hydride (3.87 mmol, 93 mg). After 1 hr of vigorous stirring, the mesylate in 10 ml of DMSO was added to this viscous mixture. The mixture became less viscous as the reaction proceeded. After stirring for 54 hrs, the mixture was poured into water (50 ml) and extracted with diethylether (3×50 ml) followed by dichloromethane (4×40 ml). After the dichloromethane was evaporated, a brown oil was formed, which, after chromatography on silica with ethylacetate, yielded 530 mg of 1-(8-nonene)-3,7-dimethylxanthine as an off-white powder (50% yield).

1-(8-nonene)-3,7-dimethylxanthine (380 mg, 1.25 mmol) was dissolved in 1 ml water and then 1 ml of concentrated sulfuric acid was added at once. This mixture was stirred for 24 hrs. The reaction mixture was poured over 50 ml water and extracted with dichloromethane (3×50 ml). The dichloromethane extractions were combined and dried over magnesium sulfate, and evaporated to yield a viscous oil. Recrystalization from minimal dichloromethane/excess diethyl ether yielded 110 mg of 1-(8-hydroxynonyl)-3,7-dimethylxanthine (0.34 mmol, 27% yield). However, this ω-1 alcohol preparation also contained a significant concentration of a contaminating ω-2 alcohol. (1-(7-hydroxynonyl)- 3,7-dimethylxanthine), which is also a compound within the scope of Formula 1.

Example 2

This example illustrates a synthesis procedure for 1-(9', 10'-dihydroxydecyl)- 3,7-dimethylxanthine racemic mixture (CT1564). The synthesis began with a solution of 9 -decene-1-ol (3.0 g, 19.2 mmol) in dichloromethane (100 ml) at 0° C. To this solution was added methanesulfonyl chloride (2.2 g, 1.5 ml, 19.2 mmol), followed by triethylamine (2.91 g, 28.8 mmol). After stirring for 15 min at 0° C., the reaction mixture was allowed to warm to room temp. After 2 hrs, the reaction mixture was poured into 100 ml of water and extracted with dichloromethane (3×60 ml). The organic portions were combined, dried in sodium sulfate, and evaporated to give 9-decene-1-mesylate as a yellow oil (4.52 g, 100% yield). The mesylate was used without further purification.

Theobromine (3.45 g, 19.2 mmol) was added to a suspension of NaH (461 mg, 19.2 mmol) in DMSO (30 ml). After 15 min, 9-decene-1-methanesulfonate (2.25 g, 11 mmol) was added and the reaction mixture was stirred for 18 hrs at 25° C., and then at 100 ° C. for 40 min. The reaction mixture was poured into 100 ml of water and extracted with dichloromethane (3×50 ml). The organic portions were combined, washed with brine (60 ml), dried with magnesium sulfate, and evaporated to provide a white solid. Recrystalization of this solid (in dichloromethane/petroleum ether) provided a colorless oil of 1-(9-decenyl)-3,7-dimethylxanthine (CT1563) 3.40 g at a 56% yield.

A solution of (1-(9-decenyl)-3,7-dimethylxanthine (3.2 g, 10.1 mmol)), 4 -methylmorpholine-N-oxide (1.41 g, 12 mmol) and $OsO_4$ (3 drops of a 2.5% solution by weight in tBuOH) in acetone (40 ml) and water (10 ml) was stirred for 24 hrs. A saturated solution of sodium dithionite (5 ml) was added to the reaction mixture which was then stirred for 15 min. The reaction mixture was extracted with 25 % EtOH/ dichloromethane (4×50 ml). The organic layers were combined, dried with sodium sulfate and evaporated to a white solid which was recrystalized in ethanol to give 1-(9,10-dihydroxydecyl)-3,7-dimethylxanthine (3.30 g, 93% yield).

Example 3

This example illustrates a synthesis for 1-(9-hydroxydecyl)-3,7-dimethylxanthine racemic mixture (CT 1552). The synthesis begins with a solution of CT1564 (2.11 g, 6.0 mmol) from Example 2. CT1564 was stirred with HBr (5.38 ml, 4.85 g of a 30% solution in acetic acid, 18 mmol) for 90 min. The mixture was added to a flask containing saturated aqueous sodium bicarbonate solution (40 ml) and 50 ml of dichloromethane. After 10 min of vigorous stirring, the layers were separated and the aqueous layers were washed with dichloromethane (2×50 ml). The organic portions were combined, dried with sodium sulfate, and evaporated to give 1-(9'-acetoxy-10'-bromodecyl)- 3,7-dimethylxanthine as a yellow oil (2.72 g, 100% yield). Without further purification, the oil was taken up in methanol (30 ml), and treated with a solution of sodium methoxide (prepared from 151 mg, 6.6 mmol sodium and 6 ml methanol). After 30 min, the reaction mixture was added to water (30 ml) and extracted with dichloromethane (3×50 ml). The organic layers were combined and dried with sodium sulfate to give an off-white solid which was recrystalized (dichloromethane/petroleum ether) to yield 1-(9,10-oxidodecyl)- 3.7-dimethylxanthine racemic mixture (CT1565).

A solution of 1-(9,10-oxidodecyl)-3,7-dimethylxanthine (200 mg, 0.6 mmol) and sodium borohydride (61 mg, 1.6 mmol) was stirred in ethanol (10 ml) at 80° C. for 4 hrs. After cooling, the reaction mixture was poured into 10 ml of saturated aqueous ammonium chloride. Water (10 ml) was added to dissolve any solids that were formed and the mixture was extracted with dichloromethane (3×50 ml). The organic extracts were combined, dried with sodium sulfate, and evaporated to an off-white solid. The solid was recrystalized (dichloromethane/petroleum ether) to give the alcohol 1-(9-hydroxydecyl)-3,7-dimethylxanthine racemic mixture (CT1552) as a white solid (180 mg, 89% yield).

Example 4

This example illustrates a synthesis procedure for 1-(8,9-dihydroxynonyl)- 3,7-dimethylxanthine (CT1561). The synthesis began by adding a solution of 8-nonene-1-ol (1.50 g, 10.5 mmol) in dichloromethane (100 ml) at 0° C. to methanesulfonyl chloride (1.20 g, 813 μl, 10.5 mmol), followed by triethylamine (1.59 g, 15.8 mmol). After stirring for 1 hr at 0° C., the reaction mixture was allowed to warm to room temperature. The reaction mixture was poured into 100 ml of water and extracted with dichloromethane (3×50 ml). The organic portions were combined, dried with sodium sulfate, and evaporated to give 9--methanesulfonyl-1-nonene as a yellow oil (2.25 g, 97% yield, which was used without further purification.

Theobromine (1.98 g, 11 mmol) was added to a suspension of NaH (600 mg of a 50% mineral oil slurry, 12 mmol) in DMSO (15 ml). After 15 min, 9-methanesulfonyl- 1-nonene (2.25 g, 11 mmol) was added and the reaction mixture was stirred for 6 days at 25 ° C. The reaction mixture was poured into 60 ml of water and extracted with dichloromethane (3×50 ml). The organic portions were combined, dried with magnesium sulfate, and evaporated to give a dark oil. Chromatography (silica, ethyl acetate) gave 1-(8 -nonenyl)-3,7-dimethylxanthine (CT1550) as a colorless oil (810 mg, 26% yield).

A solution of 1-(8-nonenyl)-3,7-dimethylxanthine (CT1550 810 mg, 2.9 mmol), 4-methylmorpholine-N-oxide (340 mg, 2.9 mmol) and $OsO_4$ (3 drops of a 2.5% solution by weight in tBuOH) in acetone (20 ml) and water (20 ml) was stirred for 24 hrs. A saturated solution of sodium dithionite (5 ml) was added to the reaction mixture which was then stirred for 15 min. The reaction mixture was extracted with 25% EtOH/dichloromethane (4×50 ml). The organic layers were combined, dried with sodium sulfate and evaporated to a white solid which was recrystalized in ethanol/chloroform to give 1-(8,9-dihydroxynonyl)-3,7-dimethylxanthine (CT 1561 ) (490 mg, 54% yield).

Example 5

This example illustrates another method for synthesizing CT1551 (in addition to the method described in Example 1). CT1561 (1-(8,9-dihydroxynonyl)-3,7-dimethylxanthine) (428 mg, 1.3 mmol) was stirred with HBr (777 μl, 1.05 g of a 30% solution in acetic acid, 3.9 mmol) for 90 min. The mixture was then added to a flask containing aqueous sodium bicarbonate solution (10 ml, 1.35 g) and dichloromethane (10 ml) and stirred vigorously for 10 min. The layers were separated and the aqueous portion was washed with dichloromethane (3×15 ml). The organic portions were combined, dried with sodium sulfate and evaporated to give 1-(8-acetoxy-9-bromononyl)-3,7-dimethylxanthine as a yellow oil (550 mg, 96% yield). Without further purification, the oil was taken up in methanol (5 ml) and treated with a solution of sodium methoxide (prepared from 33 mg, 1.4 mmol sodium and 1.4 ml methanol). After 30 min the reaction mixture was added to water (30 ml) and extracted with dichloromethane (3×40 ml). The organic portions were combined and dried to give an off-white solid which was recrystalized in dichloromethane/petroleum ether to give 1-(8,9-oxidononyl)-3,7-dimethylxanthine (CT1560) (380 mg, 91%).

CT1560 (100 mg, 0.3 mmol) was dissolved in methanol (20 ml). Palladium catalyst (10% on carbon, 100 mg) was added and the slurry was placed under hydrogen (50–55 psi) on a Parr reactor for 16 hrs. The slurry was filtered through celite, evaporated to a yellow oil and chromatographed (silica, 10% ethanol/ethyl acetate) to give CT1551 (1-(8 -hydroxynonyl)-3,7-dimethylxanthine) as a white solid (53 mg, 55% yield).

Example 6

This example illustrates a synthesis for CT1559 (1-(10-hydroxydecyl)-3,7-dimethylxanthine. A mixture of theobromine (1.0 g, 5.5 mmol) and 50% NaH in oil (264 mg, 5.5 mmol) in DMSO (35 ml) was stirred for 5 min and then 10-bromodecane-1-ol (1.3 g, 5.5 mmol) was added and stirred for 14 hrs. The solution was treated with water (100 ml) and extracted with ether (2×50 ml). The heterogeneous aqueous phase was extracted with dichloromethane (3×30 ml). The combined organic layers were washed with water (2×100 ml), dried with magnesium sulfate, and the dichloromethane was evaporated under vacuum to give CT1559 as a white powder (1.6 g, 87% yield).

Example 7

This example illustrates the effect of CT1551 and CT1559 as an immune modulator. FIG. 1 shows a mixed lymphocyte reaction of PTX and two inventive compounds CT 1551 (racemate N-(8-hydroxynonyl)theobromine) and CT1559 (N-(10-hydroxydecyl)theobromine). The mixed lymphocyte reaction shows a proliferative response of PBMC (peripheral blood mononuclear cells) to allogeneic stimulation determined in a two-way mixed lymphocyte reaction. Each of the inventive compounds tested was more effective and more potent than PTX in this immune modulating activity assay procedure.

Example 8

Figure 2:
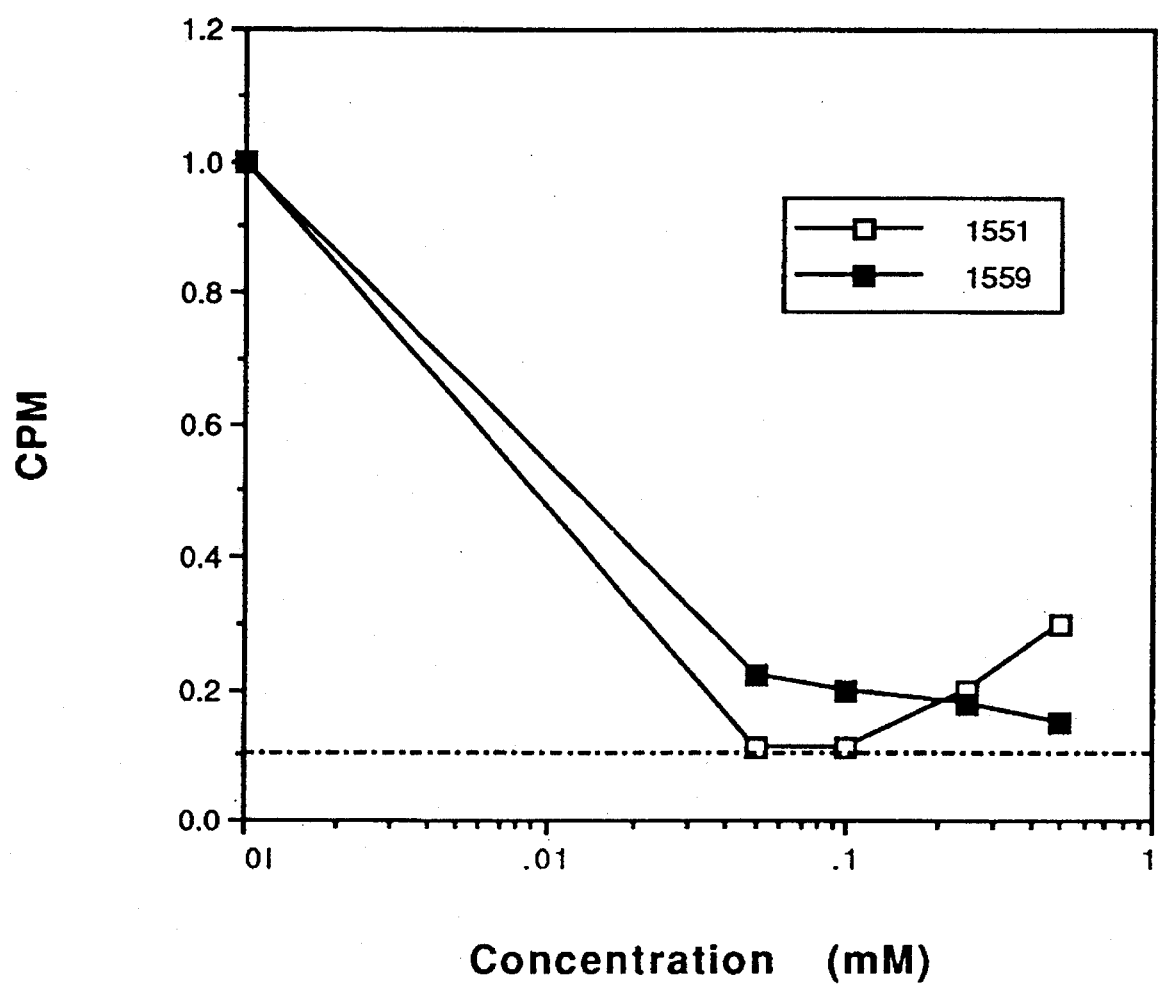
FIG. 2 shows a comparison of CT1551 and CT1559 on PDGF-induced (platelet derived growth factor) proliferation of human stromal cells. Human stromal cells were starved in serum-free media for 24 hours and then stimulated with 50 ng/ml of PDGF-BB. The drugs were added at various indicated concentrations one hour prior to PDGF stimulation. Both CT 1551 and CT 1559 inhibited PDGF-induced stimulation.

This example illustrates a comparison of CT1551 and CT1559 on PDGF-induced (platelet derived growth factor) proliferation of human stromal cells. Human stromal cells were starved in serum-free media for 24 hours and then stimulated with 50 ng/ml of PDGF-BB. The drugs were added at various indicated concentrations one hour prior to PDGF stimulation. Tritiated thymidine was added for 24 hrs at the time of PDGF stimulation. The cells were harvested and counted by liquid scintillation counting 24 hrs later. As shown in FIG. 2, both CT1551 and CT1559 inhibited PDGF-induced stimulation. Background counts (i.e., starved cells) were approximately 10% of control levels.

Example 9

Figure 3:
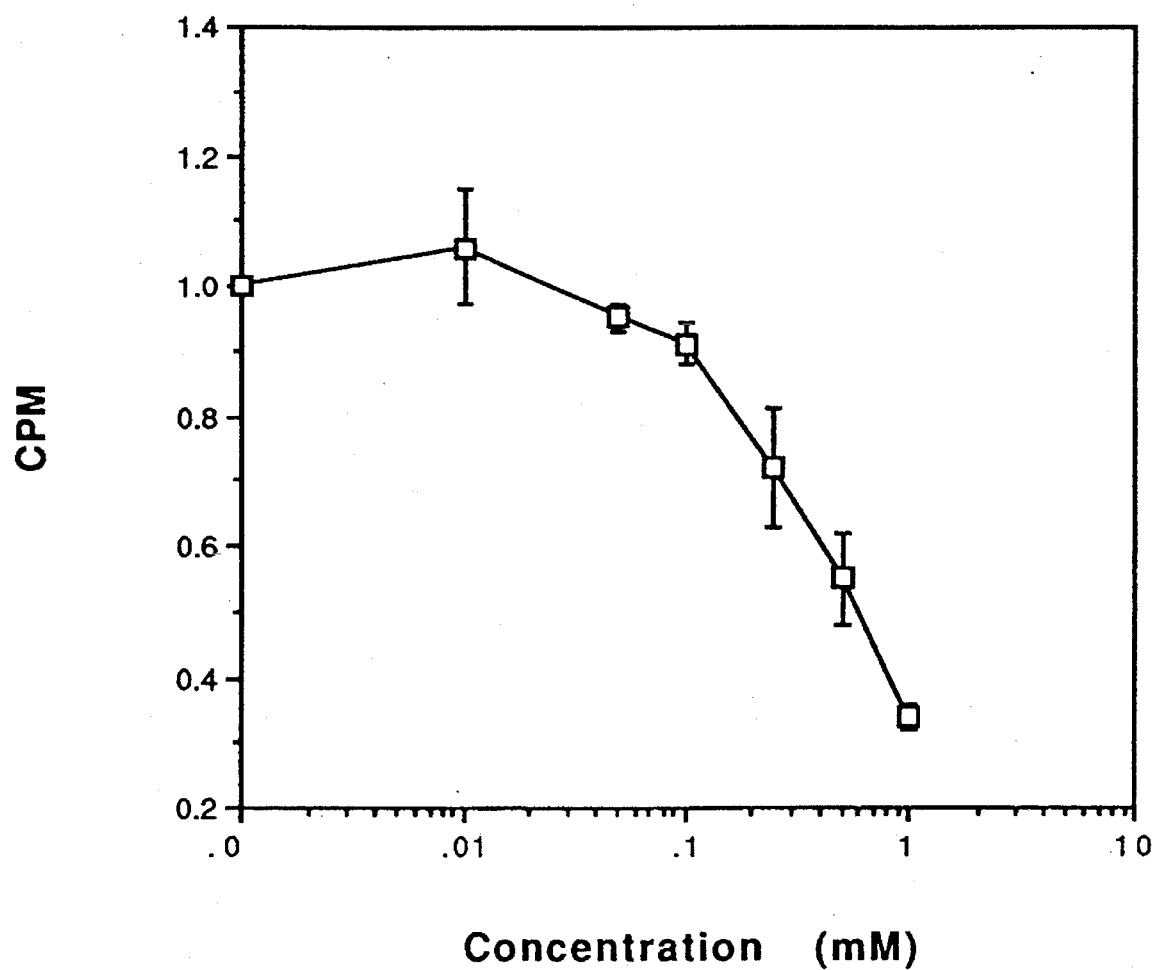
FIG. 3 shows CT 1559 cytotoxicity on LD-2 cells, a human malignant melanoma cell line. The cells were treated with various concentrations of CT1559 and later stained for cell viability with a fluorescence stain. CT1559 is cytotoxic at higher concentrations, and thus shows antitumor activity.

This example provide data from an experiment measuring CT1559 cytotoxicity on LD-2 cells, a human malignant melanoma cell line. The cells were treated with various concentrations of CT1559 and later stained for cell viability with a fluorescence stain (BCECF) and analyzed using a Milipore fluorescence plate reader. As shown in FIG. 3, CT1559 is cytotoxic at higher concentrations, and thus shows antitumor activity.

Example 10

Figure 4:
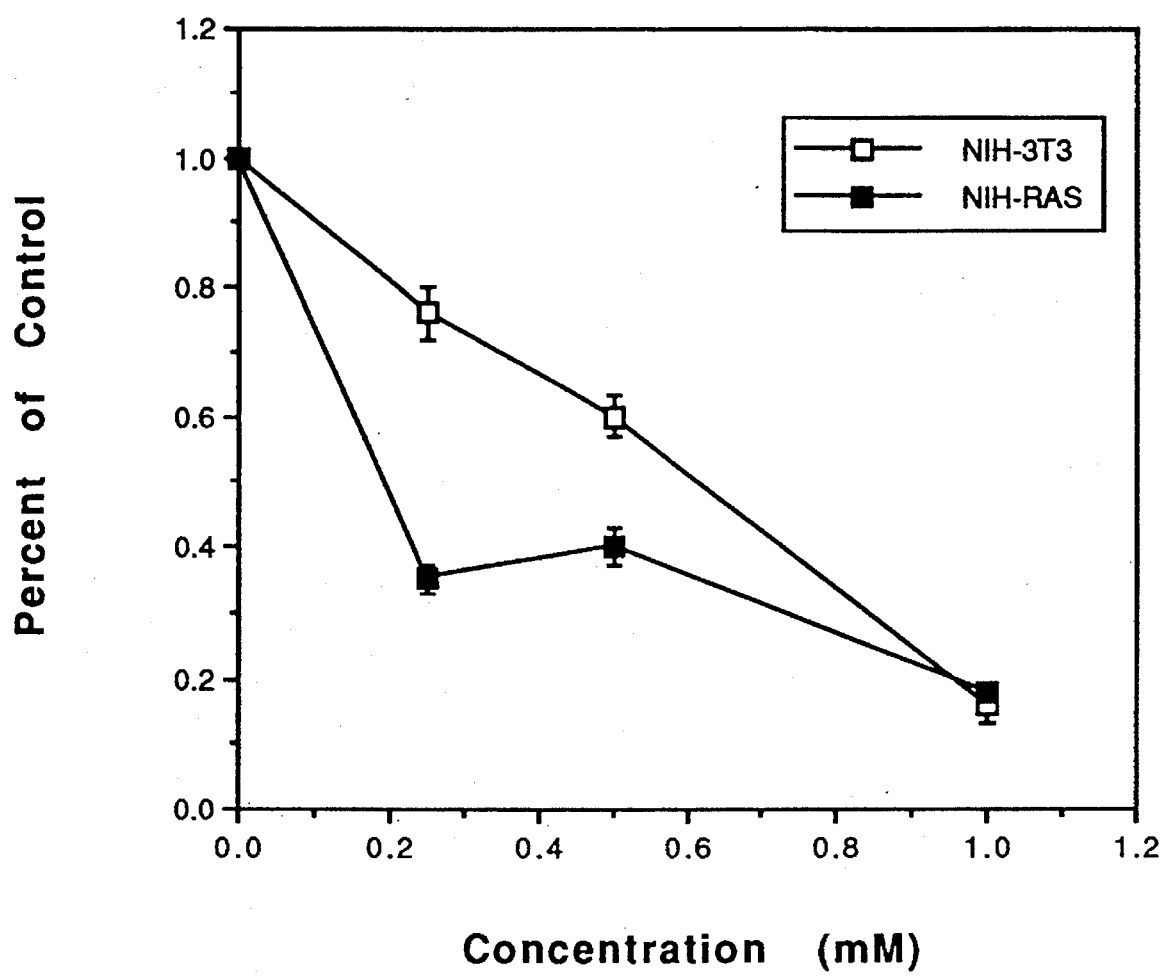
FIG. 4 shows CT1559 cytotoxicity on NIH-3T3 cells and their Ras transformed counterpart, NIH-3T3 Ras cells. The cells were treated with various concentrations of CT1559 and later stained for cell viability with a fluorescence stain. CT 1559 is cytotoxic at higher concentrations, and thus shows antitumor activity.

This example provide data from an experiment measuring CT1559 cytotoxicity on NIH-3T3 cells and their Ras transformed counterpart, NIH-3T3 Ras cells. The cells were treated with various concentrations of CT1559 and later stained for cell viability with a fluorescence stain (BCECF) and analyzed using a Milipore fluorescence plate reader. As shown in FIG. 4, CT1559 is cytotoxic at higher concentrations, and thus shows antitumor activity.

Example 11

Figure 5A:
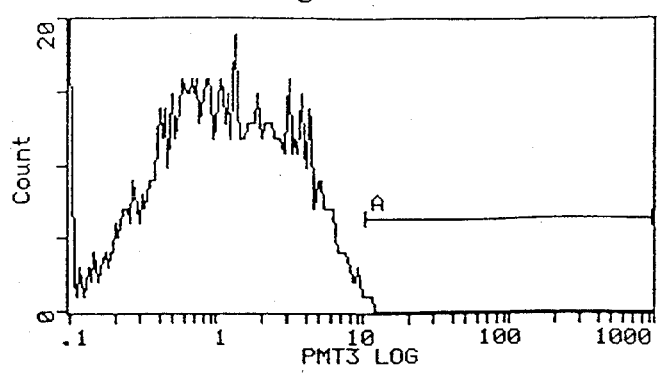
FIGS. 5A–5D show the effect of CT1559 to inhibit cell surface expression of VCAM in human umbilical vein endothelial cells (HUVEC). The HUVEC cells were stimulated with 20 ng/ml TNF-α for 20 hrs and then stained for immunofluorescence using a monoclonal antibody recognizing VCAM, followed by a goat anti-mouse antibody conjugated to phycoerythrin. The cells were analyzed for antibody binding using flow cytometry.
Figure 5B:
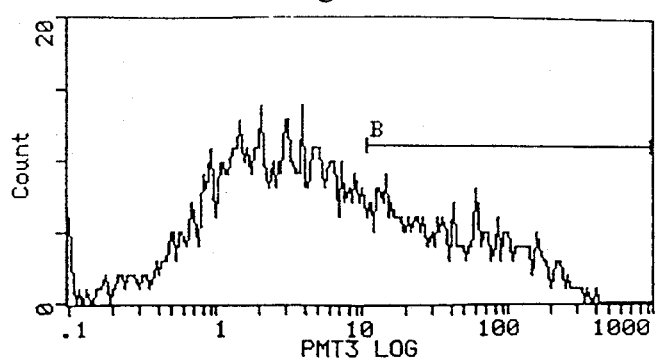
Figure 5C:
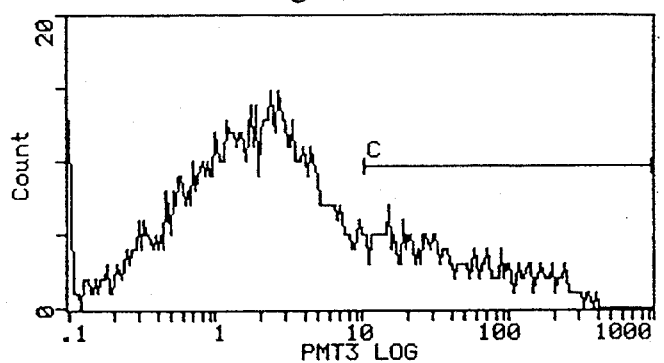
Figure 5D:
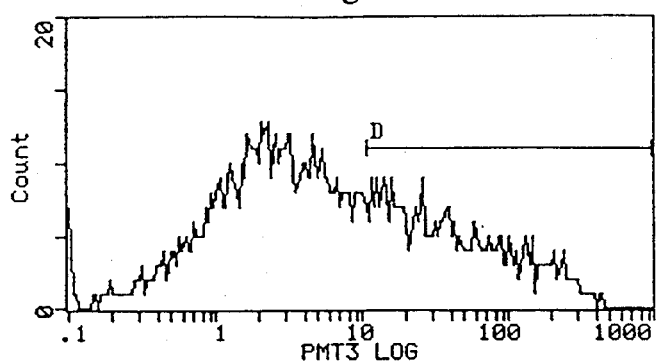

This example illustrates the effect of CT1559 to inhibit cell surface expression of VCAM in human umbilical vein endothelial cells (HUVEC). The HUVEC cells were stimulated with 20 ng/ml TNF-α for 20 hrs and then stained for immunofluorescence using a monoclonal antibody recognizing VCAM, followed by a goat anti-mouse antibody conjugated to phycoerythrin. The cells were analyzed for antibody binding using flow cytometry. FIGS. 5A–5B shows the flow cytometric frequency histograms plotting cell number versus relative fluorescence intensity. FIG. 5A is non-TNF induced expression of VCAM (% of cells in gate A is 0.4%). FIG. 5B shows cells treated with TNF (% of cells in gate B is 34.5%). FIG. 5C shows cells treated with CT1559 (0.25 mM) one hour prior to TNF addition (% of cells in gate C is 24%). FIG. 5D is cells treated with PTX for comparison (% of cells in gate D is 36.8%).

Example 12

Figure 6:
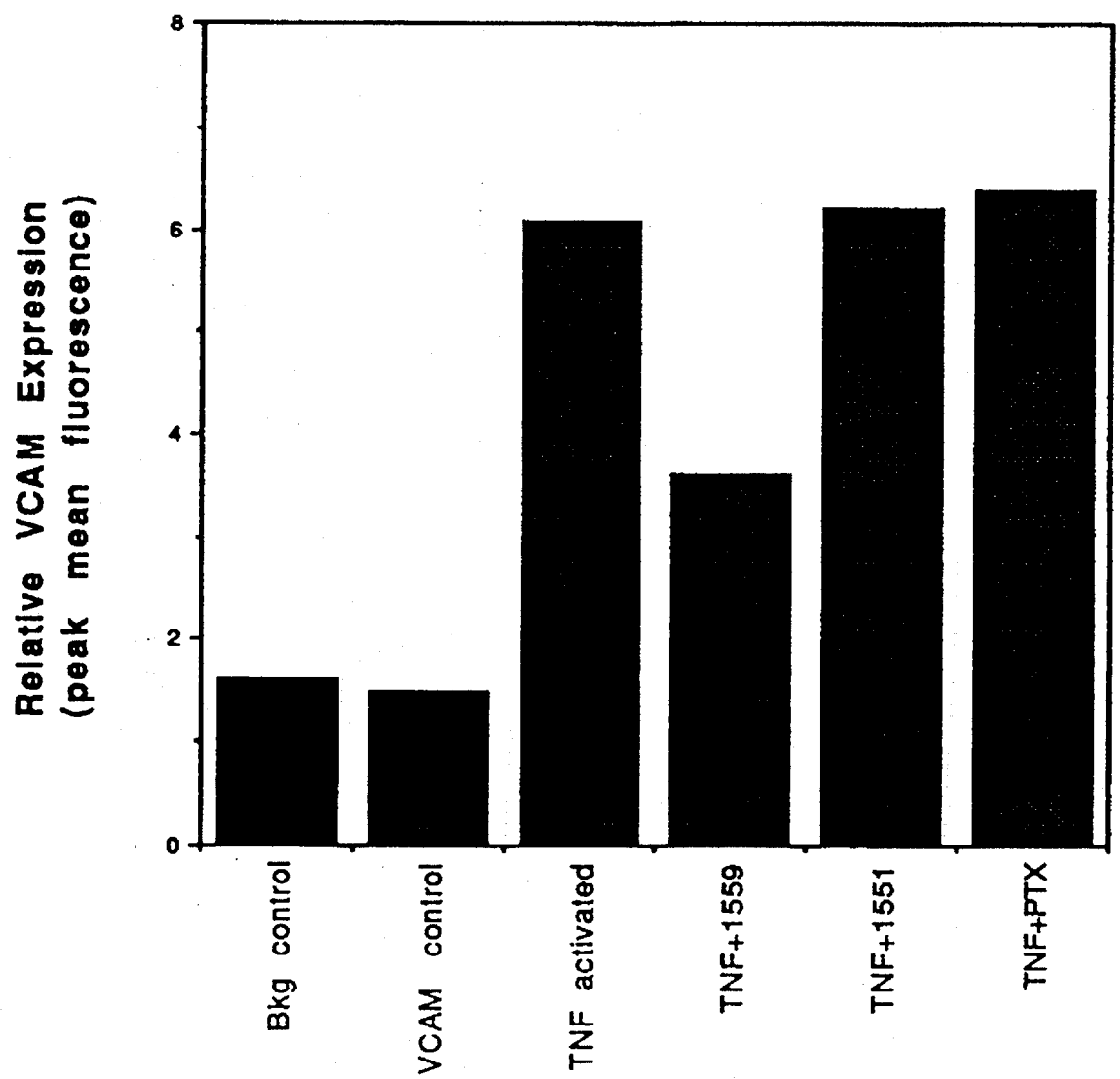
FIG. 6 shows the effect of CT1559 to inhibit cell surface expression of VCAM in HUVEC cells. The cells were stimulated with TNF-α (20 ng/ml) for 20 hrs and then stained for immunofluorescence using a monoclonal antibody recognizing VCAM, followed by a goat anti-mouse antibody conjugated to phycoerythrin. The cells were analyzed for antibody binding using flow cytometry.

This example illustrates the effect of CT1559 to inhibit cell surface expression of VCAM in HUVEC cells. The cells were stimulated with TNF-α (20 ng/ml) for 20 hrs and then stained for immunofluorescence using a monoclonal antibody recognizing VCAM, followed by a goat anti-mouse antibody conjugated to phycoerythrin. The cells were analyzed for antibody binding using flow cytometry for antibody binding. FIG. 6 shows an analysis of mean fluorescence intensity of cells analyzed by flow cytometry. The mean fluorescence levels were decreased by CT1559 treatment by 1.7 fold from control levels (TNF treatment, no drug).

Example 13

This example illustrates a comparison of MLR (mixed lymphocyte reaction) data of xanthine derivative compounds of varying chain lengths from the 1 position on a ring nitrogen of xanthine to show a comparison of biological activity as a function of chain length. A mixed lymphocyte reaction was run with a series of substituted xanthine compounds having an alcohol substituent on the N1 ring nitrogen of xanthine. The mean IC50 of each compound was determined. Table 1 lists the results found:

| Compound | Chain Length | Mean IC50 (μM) | Formula 1 | Alcohol |
|---|---|---|---|---|
| CT1551 | 9 | 120 | Y | secondary |
| CT1559 | 10 | 150 | Y | primary |
| CT1561 | 9 | 185 | Y | diol |
| CT1564 | 10 | 210 | Y | diol |
| CT1501 | 6 | >500 | N | primary |
| CT1502 | 6 | >500 | N | diol |
| CT1536 | 8 | 250 | N | secondary |
| CT1538 | 8 | >500 | N | diol |
| CT1540 | 3 | >500 | N | diol |
| CT1542 | 5 | >500 | N | secondary |
| CT1545 | 7 | 300 | N | primary |
| CT1546 | 8 | 320 | N | primary |
| CT1556 | 6 | >500 | N | primary |

Accordingly, these data show the importance of chain length for immune modulating activity in the MLR assay.

We claim:

1. A compound of the formula:

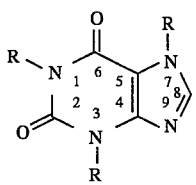

FORMULA 1 wherein at least one R is

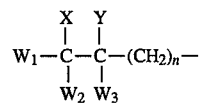

wherein n is an integer from 7 to 20, at least one of X or Y is —OH and if one of X or Y is —OH then the other X or Y is H, $CH_3$, $CH_3$—$CH_2$, $CH_3$—$(CH_2)_2$—, or $(CH_3)_2$—$CH_2$—, and $W_1$, $W_2$, and $W_3$ are independently H, $CH_3$, $CH_3$—$CH_2$, $CH_3$—$(CH_2)_2$—, or $(CH_3)_2$—$CH_2$—, and wherein the alkyl groups may be substituted by a hydroxyl, halo or dimethylamino group and/or interrupted by an oxygen atom, H or alkyl (1–4C), and the other one or two R's are independently H or $CH_3$, including resolved enantiomers and/or diastereomers, salts and mixtures thereof.

2. The compound of claim 1 wherein the R is at position 1 of the xanthine ring.

3. The compound of claim 1 wherein the Rs at positions 3 and 7 are methyl.

4. The compound of claim 1 wherein both X and Y are OH.

5. The compound of claim 1 wherein each W is H or methyl.

6. The compound of claim 1 wherein n is 7–10.

7. A pharmaceutical composition comprising a compound selected from the group consisting of N-(8-hydroxynonyl)theobromine, N-(9-hydroxydecanyl)theobromine, N-(10-hydroxydecanyl)theobromine, N-(8,9-dihydroxynonyl)theobromine, N-(9,10-dihydroxydecyl)theobromine and combinations thereof, and a pharmaceutically acceptable excipient.

8. The pharmaceutical composition of claim 7 further comprising an effective amount of an anti-P-450 agent, in admixture with a pharmaceutically acceptable excipient.

9. The pharmaceutical composition of claim 8 wherein the anti-P-450 agent is a quinolone.

10. A pharmaceutical composition comprising the compound of claim 1 in admixture with at least one pharmaceutically acceptable excipient.

11. The pharmaceutical composition of claim 10 further comprising an effective amount of an anti-P-450 agent.

12. The pharmaceutical composition of claim 11 wherein the anti-P-450 agent is a quinolone.

* * * * *